United States Patent
Mehlo et al.

(10) Patent No.: US 8,143,484 B2
(45) Date of Patent: Mar. 27, 2012

(54) METHOD FOR REGULATING AGROBACTERIUM-MEDIATED TRANSFORMATION

(75) Inventors: Luke Mehlo, Pretoria (ZA); Zuo-Yu Zhao, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 470 days.

(21) Appl. No.: 12/357,284

(22) Filed: Jan. 21, 2009

(65) Prior Publication Data

US 2009/0263902 A1 Oct. 22, 2009

Related U.S. Application Data

(60) Provisional application No. 61/022,981, filed on Jan. 23, 2008.

(51) Int. Cl.
*C12N 15/84* (2006.01)
(52) U.S. Cl. .......................... 800/294; 800/320; 435/469
(58) Field of Classification Search .................. None
See application file for complete search history.

(56) References Cited

U.S. PATENT DOCUMENTS

| | | |
|---|---|---|
| 5,641,644 A | 6/1997 | Klebe |
| 5,712,135 A | 1/1998 | D'Halluin et al. |
| 6,002,070 A | 12/1999 | D'Halluin et al. |

OTHER PUBLICATIONS

Grimsley et al. Bio/Technology 6: 185-189 (Feb. 1988).*
Grimsley et al. Molecular and General Genetics 217: 309-316 (1989).*
Lo et al. Physiological and Molecular Plant Pathology 61(3): 179-188 (Sep. 2002).*
Roy et al., Curr. Scie. (2000) 79:954-960.
Shimoda et al., PNAS USA (1990) 87:6684-6688.
Spencer and Towers, Phytochem. (1988) 27:2781-2785.
Zhao et al., Plant Mol. Biol. (2000) 44:789-798.
Zhu et al., J. Bacteriol. (2000) 182:3885-3895.
Carvalho et al., Genetics and Molecular Biology (2004) 27(2):259-269.
Gao et al., Plant Biotechnology Journal (2005) 3:591-599.
Howe et al., Plant Cell Rep (2006) 25:784-791.
International Search Report for PCT/IB2009/050261, mailed Jul. 16, 2009, 4 pages.
Nguyen et al., Plant Cell Tiss Organ Cult (2007) 91:155-164.

* cited by examiner

*Primary Examiner* — David T Fox
(74) *Attorney, Agent, or Firm* — Morrison & Foerster LLP

(57) ABSTRACT

A method for regulating expression of a virulence gene of *Agrobacterium* is described. The method comprises the steps of stimulating cereal cells, such as sorghum, so as to produce an active, typically phenolic, compound and exposing the *Agrobacterium* to this compound. The compound induces expression of the virulence gene of the *Agrobacterium*, effecting T-DNA transfer from the *Agrobacterium* to the cereal cells, which are thereby transformed.

19 Claims, 4 Drawing Sheets

METHOD FOR REGULATING AGROBACTERIUM-MEDIATED TRANSFORMATION

CROSS-REFERENCE TO RELATED APPLICATIONS

This application claims priority from U.S. provisional application 61/022,981 filed Jan. 23, 2008. The contents of this document are incorporated herein by reference.

BACKGROUND OF THE INVENTION

This invention relates to a method for regulating expression of at least one virulence gene of *Agrobacteria*. In particular, this invention relates to the stimulation of embryonic cereal cells for the production of phenolic and/or other compounds. In addition, this invention relates to the use of the secreted phenolic and/or other compounds for activation of the vir-operon of *Agrobacteria* resulting in transformation of the embryonic cereal cells.

*Agrobacterium tumefaciens* has been extensively exploited as an important gene delivery tool for most of the families of higher plants. Under laboratory conditions, it has been shown that the host range of *Agrobacterium* can be extended to include virtually any living cell, for example, other prokaryotes like *Streptomyces lividans*, yeast, fungi and cultured human cells.

*Agrobacterium* achieves the transformation of its hosts by transferring a well defined segment of DNA (called transfer DNA (T-DNA)) from its tumour inducing (Ti) plasmid to host cells. The transfer process requires a number of components: chromosomal and Ti plasmid-encoded gene products. Virulence (vir) genes are contained within the Ti (tumour inducing) plasmid and encode proteins required for processing and transfer of T-DNA.

With respect to plant transformation, the vir region of the Ti-plasmid is activated by a two component system, Vir A/Vir G and a galactose binding protein ChvE in response to phenolic compounds and sugars exuded from wounded plant cells. In a manner similar to bacterial two-component systems, Vir A, a periplasmic membrane-spanning protein, senses the phenolic compound(s)/simple monosaccharide stimuli and autophosphorylates at its histidine residue in the cytoplasmic C-terminus. The Vir G protein is considered to act as a signal-response regulator, because after receiving a phosphate (through transphosphorylation) from the Vir A phospho-histidine (Vir A sensor kinase), it activates transcription of the vir genes by binding to the vir boxes in the promoters of vir genes and activates their gene expression. This enables the processing and transport of the T-DNA through a T-pilus-associated type IV secretion system (T4SS) from *Agrobacterium* into the plant nuclear genome where the T-DNA is integrated into chromosomal DNA, thus completing the transfer of any transgenes that might have been cloned within the T-DNA boarders of *Agrobacterium tumefaciens*.

Acetosyringone, a plant cell wound product, is one of the major plant phenolic inducers of the two-component Vir A/Vir G system in *Agrobacterium tumefaciens*. Other secreted plant diffusible factors which induce T-DNA circularization and vir gene expression have been identified and include small (<100 Da) diffusible plant metabolites produced by actively metabolizing plant cells, catecol, sugars and amino acids. Many of these factors are produced both in monocotyledonous and dicotyledonous plants, and this partially explains why some monocotyledonous plants are susceptible to *Agrobacterium tumefaciens*. There is, however, a distinction between the ability of these factors to act as chemo-attractants to *Agrobacterium* (a phenomenon that brings the bacterium within close proximity to susceptible host cells) and the ability to induce vir gene expression, which is required for T-DNA transfer. Chemo-attraction is very sensitive and occurs at low molar concentrations of the diffusible products, whereas higher concentrations (as occurs in the proximity of secreting cells) of the products are required to induce vir gene expression. This perhaps explains why many monocotyledonous plants have been regarded as recalcitrant to *Agrobacterium tumefaciens*-mediated transformation, and often require supplementation with synthetic acetosyringone when *Agrobacterium* is employed as a preferred vehicle for transformation. In rice, for example, supplementation with acetosyringone is required and contributes to higher T-DNA transfer if used at the early initial stages of bacterial infection and also during co-cultivation. For wheat, higher amounts of acetosyringone (200 μM instead of the usual 100 μM) lead to higher levels of T-DNA transfer and transformation efficiency. Studies with barley revealed that the effects of acetosyringone on transformation efficiency are dependent on the plant species concerned. In the case of barley, acetosyringone concentrations in the range between 200-1000 mg/l (higher than for rice) can be used effectively. There are a few exceptions within monocotyledonous plants, depending on the target explant tissue used for transformation, where the addition of acetosyringone may not be effective. In lillies (ornamental monocotyledonous plants), for example, the addition of acetosyringone does not have any effect on transformation efficiency. Generally, it is well documented that wounded dicotyledonous plant tissues produce phenolic compounds such as acetosyringone (4-acetyl-2,6-dimethoxyphenol), and that monocotyledonous plants may fall into two categories: those that do not produce phenolic compounds and those which may produce acetosyringone despite the levels being so low as not to affect vir gene induction.

In certain instances, acetosyringone alone may not efficiently induce vir genes in *Agrobacterium tumefaciens*. It has been shown that when the concentration of acetosyringone is limited (as occurs in some monocotyledonous plants), a group of aldoses (for example: L-arabinose, D-xylose, D-glucose, D-mannose, D-idose, D-galactose and D-talose) can effectively enhance acetosyringone-dependent expression of vir genes. This suggests that other factors, sugars in this particular case, directly enhance a signaling process initiated by phenolic inducers to result in an increase in the expression of vir genes of *Agrobacterium*. The protein ChvE, which binds glucose-galactose and interacts with the vir A protein, was specifically identified and implicated in broadening the phenolic recognition profiles of *Agrobacterium* vir A protein and hence vir gene expression, especially when it was available at high levels. Other enhancers of vir gene expression include phosphate starvation and acidic culture medium. When acetosyringone alone is used to induce vir gene expression, *Agrobacterium* transformation efficiency for sorghum is very low, even when the current best protocols are used (Zhao et al., 2000. Plant Mol. Biol. 44: 789-798).

U.S. Pat. No. 5,641,644 teaches a method for reproducibly and efficiently transforming the genome of a monocotyledonous plant, and in particular a gramineous plant such as a cereal. This disclosure concentrates on the use of compact embryogenic callus or intact tissue capable of forming compact embryogenic callus. Transformation by this method is, however, limited to electroporation and is silent regarding *Agrobacterium*-mediated transformation. Furthermore, no mention is made regarding the use of endogenous compounds to facilitate and enhance transformation.

The methodology taught in U.S. Pat. No. 5,641,644 was subsequently extended to cereal crops in general (U.S. Pat. No. 5,712,135), and specifically to rice (U.S. Pat. No. 6,002, 070).

The applicants have therefore identified a need to increase the *Agrobacterium*-mediated transformation efficiency of cereals, especially sorghum.

SUMMARY OF THE INVENTION

According to a first embodiment of the invention, there is provided a method for regulating expression of at least one virulence gene of *Agrobacterium*, the method comprising the steps of:

stimulating cereal cells to produce at least one active compound; and contacting or exposing the *Agrobacterium* to the active compound(s).

The *Agrobacterium* is typically *Agrobacterium tumefaciens*.

The expression of the virulence gene, for example the virA and/or virG gene, is preferably up-regulated so as to induce and/or enhance transformation of cereal cells exposed to the *Agrobacterium* and active compound(s).

The active compound produced by the stimulated cereal cells may be phenolic compound(s).

The cereal cells which are stimulated to produce the active compound(s) may be sorghum cells.

The cereal cells which are transformed may be sorghum cells, or alternatively may be non-sorghum cells such as maize, wheat, barley, millet and/or rice.

The method may be performed without the addition of exogenous acetosyringone, sinapinic acid, syringic acid, vanillin, ferulic acid, 3,4 dihydroxy-benzoic acid, catechol, p-hydroxy-benzoic acid, vanyllyl alcohol, 3,4 dihydroxy-benzalhyde, vanillic acid and isovanillic acid.

Alternatively, the method may be performed in the presence of at least one of exogenous acetosyringone, sinapinic acid, syringic acid, vanillin, ferulic acid, 3,4 dihydroxy-benzoic acid, catechol, p-hydroxy-benzoic acid, vanyllyl alcohol, 3,4 dihydroxy-benzalhyde, vanillic acid and isovanillic acid; and/or at least one exogenous aldose such as L-arabinose, D-xylose, D-glucose, D-mannose, D-idose, D-galactose and/or D-talose.

The cereal cells may be mature or immature embryonic cells.

The cereal cells may be stimulated to produce the active compound by wounding, centrifuging, sonicating, heat shocking, vortexing and/or chemically wounding the cells.

According to a second embodiment of the invention, there is provided an *Agrobacterium*-mediated method for transforming plant cereal cells, the method comprising the steps of:

stimulating cereal cells to produce at least one active compound; and exposing the *Agrobacterium* to the cereal cells and the active compound(s) produced by the cereal cells, such that the active compound induces expression of at least one virulence gene of the *Agrobacterium* and effects T-DNA transfer from the *Agrobacterium* to the cereal cells, thereby transforming the cereal cells.

The cereal cells which are stimulated to produce the active compound(s) may be sorghum cells. Non-sorghum cereal cells (such as maize, wheat, barley, millet and rice) may also be exposed to the *Agrobacterium* and active compound(s) produced by the sorghum cells and thereby also transformed.

The method may be substantially as described above.

According to a third embodiment of the invention, there is provided the use of at least one active compound, which has previously been identified by stimulating sorghum cells, in an *Agrobacterium*-mediated method for transforming plant cereal cells, the method comprising the step of exposing the *Agrobacterium* to the cereal cells and the active compound(s), such that the active compound induces expression of at least one virulence gene of the *Agrobacterium* and effects T-DNA transfer from the *Agrobacterium* to the cereal cells, thereby transforming the cereal cells.

DETAILED DESCRIPTION OF THE INVENTION

Figure 1:
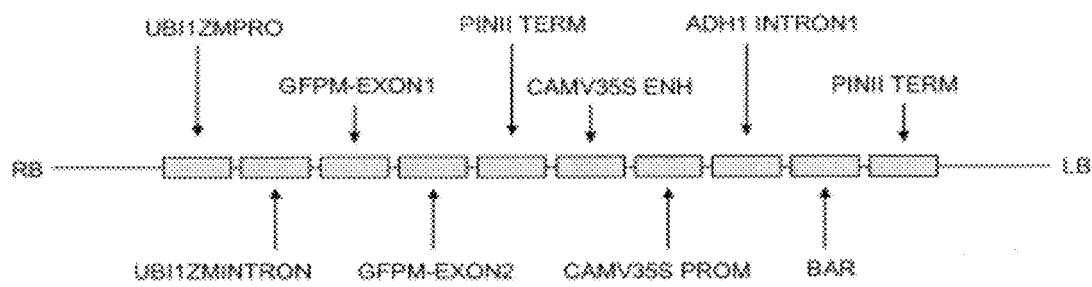
FIG. 1: Schematic diagram of the plasmid PHP15303 used for *Agrobacterium* transformation. This plasmid contains the visual marker, gfp gene driven by the maize Ubiquitin promoter and the selectable marker, bar gene driven by the 35S promoter. UBI1ZMPRO=Maize Ubiquitin promoter; UBI1ZMINTRON=maize ubiquitin 1 intron; GFPM-EXON1 & 2=exon 1 or 2 for green fluorescence gene; PINII TERM=pin II terminator sequence; CAMV35S ENH=Cauliflower mosaic virus 35 S enhancer sequence; CAMV35S PROM=Cauliflower mosaic virus 35 S promoter; ADH1 INTRON1=Alcohol dehydrogenase intron 1 sequence; BAR=selectable marker bar gene for phosphinothricin (PPT) resistance. RB=right boarder sequence for *Agrobacterium tumefaciens*; LB=left boarder sequence for *Agrobacterium tumefaciens*.

Disclosed is a method for regulating the expression of at least one virulence gene of the vir operon of *Agrobacterium* sp., in particular, the activation of the vir-operon of *Agrobacterium tumefaciens* and T-DNA transfer for the purpose of genetic transformation in plants.

Briefly, the present invention relates to a novel method for the activation of the vir-operon of *Agrobacterium* sp. The method comprises stimulating embryonic cereal cells to produce phenolic compounds and contacting the embryogenic cells with *Agrobacterium* sp.

The applicants have shown that sorghum cells can be stimulated to produce phenolic compounds or factors, such as by wounding immature embryos of sorghum. These phenolic compounds or factors were shown to influence T-DNA transfer, not only in sorghum, but also in other cereals such as maize (corn), as described below. The endogenous phenolic compounds or factors produced by the sorghum cells can be used to substitute for the exogenous phenolic compound, acetosyringone, which is usually added to the infection and co-cultivation medium used for *Agrobacterium*-mediated transformation of plants. Thus, it may not be necessary to add acetosyringone to the transformation medium. Alternatively, the phenolic compounds produced by the sorghum cells could be used in combination with exogenous acetosyringone to enhance the effect of the exogenous acetosyringone. The term "endogenous" is used herein to indicate that the compounds or factors are produced by the plant cells rather than being added to the transformation medium by an external source, whereas the term "exogenous" is intended to indicate that a compound is obtained from an external source and added to the transformation medium, rather than being produced by the plant cells.

Compared to the exogenous acetosyringone which is usually added to the transformation medium, the endogenous phenolic compounds or factors produced according to the method of the invention confer a T-DNA transfer frequency of about 15% higher than the exogenous acetosyringone at the transient level. Stably transformed callus and plants obtained in the absence of exogenous acetosyringone in the infection and co-cultivation medium indicated that endogenous phenolic compounds engendered permanent transmission of T-DNA into chromosomal/genomic DNA of plants. A broad application of this method of transformation and materials would be to use phenolic compounds or factors thus identified to broaden the scope for significantly improving the efficiency of *Agrobacterium*-mediated transformation, not only in sorghum, but in many other cereal crops, such as corn, wheat, barley and rice.

Materials, factors and methods for inducing vir operon (and hence vir gene) expression in *Agrobacterium tumefaciens* are described herein. The applicants have shown that phenolic compounds or factors exuded by cultured immature sorghum embryos are potent inducers of vir gene expression during the infection and co-cultivation phases when *Agrobacterium* is used to transform immature embryos of sorghum. This involved infecting sorghum immature embryos and co-cultivating them in the absence of the exogenous phenolic compound acetosyringone. Further, the applicants have shown that phenolic compounds and/or factors produced by wounded cultured embryos of sorghum can be used to induce and enhance vir gene expression, and effect efficient transient and stable T-DNA transfer in maize.

From these results, it is possible that phenolic compounds produced by wounded immature embryos of sorghum can be efficiently employed and used to enhance or substitute for acetosyringone or other transformation-inducing compounds when *Agrobacterium* is used for transforming other cereal crops such as corn, rice, wheat and barley. The current repertoire of known phenolic compounds which can be used to induce *Agrobacterium* transformation, albeit to different levels of efficiency, includes but is not limited to: acetosyringone, sinapinic acid, syringic acid, vanillin, ferulic acid, 3,4 dihydroxy-benzoic acid, catechol, p-hydroxy-benzoic acid, vanyllyl alcohol, 3,4 dihydroxy-benzalhyde, vanillic acid and isovanillic acid.

The method and compounds or factors described in the present invention are unique in that virulence-inducing acetophenones, such as acetosyringone, are thought to be restricted to families in, or close to Solanaceae, or that if present in monocotolydenous plants, they are produced to such low levels as not to have significant influence on transformation efficiency (Roy, et. al., 2000. Curr. Scie. 79: 954-960). This is the first time that compounds derived from sorghum have been used to substitute for, or to enhance, *Agrobacterium* vir gene expression and T-DNA transfer in crops or plants, as exemplified by sorghum and maize in the present disclosure.

The invention will now be described in more detail by way of the following non-limiting examples.

EXAMPLES

Plant Materials and Media Compositions

The sorghum public line, P898012 (originally supplied to Pioneer Hi-Bred International-USA by Dr. John Axtell, Purdue University; see Zhao et al., 2000) and the maize genotype denoted GS3 (developed by Pioneer Hi-Bred International-USA) were used for the isolation of immature zygotic embryos at 9-14 days after pollination. The two genotypes were grown in Pioneer greenhouses primarily as described in Zhao et al., 2000. Sterilization of sorghum panicles and corn ears was carried out with 50% Chlorox Bleech (3.075% (v/v) sodium hypochlorite) and 0.1% (v/v) Tween 20 for 20 minutes and then rinsed three times with sterile distilled water. This sterilization procedure was repeated with 10% Chlorox bleech (0.615% (v/v) sodium hypochlorite). Immature zygotic embryos ranging in size from 0.8 mm-1.8 mm were isolated and treated as indicated in the transformation procedures outlined below. The compositions of various media used in this study are outlined in Table 1.

TABLE 1

Media compositions

| Media and usage | Composition |
| --- | --- |
| 700: liquid media used for *Agrobacterium* infection of immature embryos (GS3, P898012) | The following components were dissolved sequentially in 950 ml polished de-ionized water: 4.3 g MS basal salt mixture; 0.1 g Myo-Inositol (10 000X); 0.5 ml Nicotinic acid (1 mg/ml stock); 0.5 ml Pyridoxine (1 mg/ml stock); 2.5 ml Thiamine HCl. (4 mg/ml); 1 g Vitamin Casamino acids; 68.5 g Sucrose; 36 g glucose PH adjusted to 5.2 with 1M KOH. Final volume adjusted to 1 L with polished de-ionized water The media filter sterilized through a 0.22 μm filter and aliquoted into 12 ml volumes and stored at 4° C. Quality control tests carried out by streaking a few microlitres of the media onto microbial plates to check for |

TABLE 1-continued

Media compositions

| Media and usage | Composition |
|---|---|
| 710B: Co-cultivation medium | contamination over 3 days.<br>The following components were dissolved sequentially in 950 ml polished de-ionized water: 4.3 g MS basal salt mixture; 0.1 g Myo-Inositol; 0.5 ml Nicotinic acid (1 mg/ml stock); 0.5 ml Pyridoxine (1 mg/ml stock); 2.5 ml Thiamine HCl. (4 mg/ml); 4 ml 2,4-D (0.5 mg/l stock); 20 g Sucrose; 10 g glucose; 0.7 g L-proline; 0.5 g MES buffer.<br>PH adjusted to 5.8 with 1M KOH.<br>Final volume adjusted to 1 L with polished de-ionized water<br>4 g Sigma agar added<br>Autoclaved and cooled to 45-55° C.<br>Add 1 ml (100 mM stock) filter sterilized acetosyringone<br>Add 1 ml (10 mg/ml) Ascobic acid<br>Mix and pour plates<br>Quality control tests carried out by streaking a few microlitres of the media onto microbial plates and incubating at 28° C. to check for contamination over 3 days. |
| 720J: First two weeks PPT selection (for transformations carried out with the bar gene) | The following components were dissolved sequentially in 950 ml polished de-ionized water: 4.3 g MS basal salt mixture; 0.5 ml Nicotinic acid (1 mg/ml stock); 0.5 ml Pyridoxine (1 mg/ml stock); 2.5 ml Thiamine HCl. (4 mg/ml); 0.1 g Myo-Inositol; 3 ml 2,4-D (0.5 mg/l stock); 20 g Sucrose; 0.7 g L-proline; 0.5 g MES buffer.<br>PH adjusted to 5.8 with 1M KOH.<br>Final volume adjusted to 1 L with polished de-ionized water<br>4 g Sigma agar added<br>Autoclaved and cooled to 60° C.<br>1 ml added of Ascobic acid (10 mg/ml)<br>2 ml Agribio carbenicillin (50 mg/ml) added<br>5 ml PPT (10 mg/ml Glufosinate -$NH_4$)<br>Mix and pour plates<br>Quality control carried out by streaking a few microlitres of the media onto microbial plates and incubating at 28° C. to check for contamination over 3 days. |
| 720K | Essentially similar to 720J except that 10 ml PPT (10 mg/ml Glufosinate -$NH_4$) was used instead of 5 mg/l PPT |
| 289J | The following components were dissolved sequentially in 950 ml polished de-ionized water: 4.3 g MS basal salt mixture; 1.0 g Myo-Inositol; 5 ml of MS Vitamin stock solution; 1 ml zeatin (of stock 0.5 mg/ml); 0.7 g L-Proline; 60 g sucrose;<br>PH adjusted to 5.6 with 1M KOH.<br>Final volume adjusted to 1 L with polished de-ionized water<br>4 g Sigma agar added<br>Autoclaved and cooled to 60° C.<br>After autoclaving add; 2.0 ml of IAA (0.5 mg/ml stock); 1.0 ml ABD (0.1 mM stock); 0.1 ml of Thidiazuron (1.0 mg/ml stock); 2.0 ml carbenicillin (50 mg/ml stock); 5.0 ml PPT (1.0 mg/ml stock of Glufosinate-NH4).<br>Mix and pour plates<br>Quality control carried out by streaking a few microlitres of the media onto microbial plates and incubating at 28° C. to check for contamination over 3 days. |

Transformation Procedures and Identification of Putative Positive Transformants

*Agrobacterium tumefaciens*

Transformation was carried out in 6 distinctive but sequential phases. The medium used at each phase is given in Table 1 above.

1. Freshly isolated embryos of P898012 or GS3 were mixed together or separated into 1.5 mL of medium 700 either lacking or containing 100 mM or 200 mM acetosyringone. The concentration of *A. tumefaciens* harbouring the vector PHP15303 (FIG. 5) in the suspension was adjusted to $0.857 \times 10^9$ cfu/mL [Optical Density (OD) approximately 0.6 at 550 nm]. The infection suspension was vortexed gently for 15 seconds, poured into 1 cm-diameter microplates and vacuumed for 5 minutes with gentle rocking for mixing.

2. The *Agrobacterium* suspension was then aspirated and the embryos plated on co-cultivation medium 710B either lacking or containing 100 mM and 200 mM acetosyringone for 3 days (co-cultivation) and cultured in the dark at 25° C.

3. After the 3-day co-cultivation, the embryos were transferred onto resting medium 710B containing 100 mg/mL carbenicillin, an antibiotic to kill off the *Agrobacterium*. This medium did not contain acetosyringone. The embryos were cultured in the dark for 4 days at 28° C. during this phase.

4. The embryos were then transferred onto medium 720J for two weeks in the dark at 28° C.
5. The proliferating embryos were then subjected to a second phase of selection on medium 720K until putative transgenic callus units averaging about 1 cm in diameter were observed.
6. Putative transgenic calli were regenerated on medium 289J.

The transformation process is summarised below:

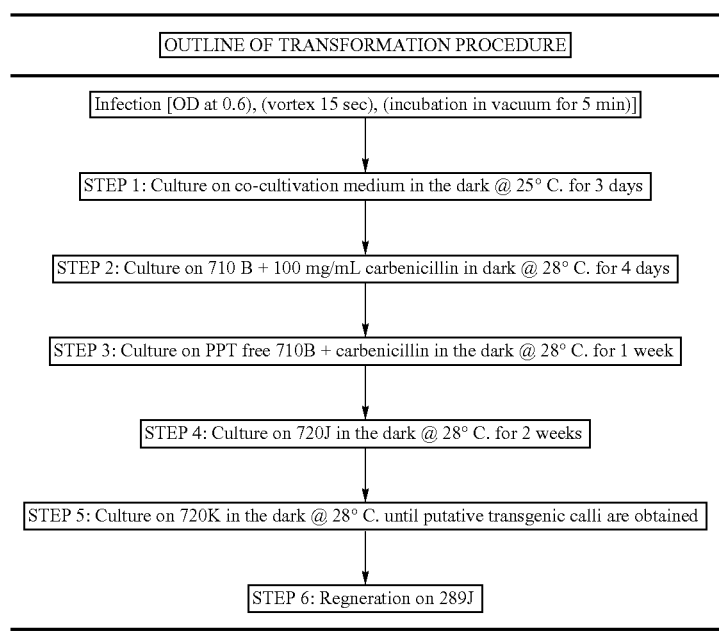

Imaging for green fluorescent protein (GFP) expression (contained as a visual marker within vector PHP15303 (FIG. 1) to enable confirmation of integration of the gene of interest into the genome of the host and expression of the gene in the host cell) was carried out starting at two days post infection until stable integration was achieved (normally over 30 days post infection). Fresh subcultures were conducted at 1-2 week intervals depending on the amount of observable phenolic compounds or other compounds on the medium. Putative transgenic calli from one embryo were kept separate and tentatively treated as one event until proven through analysis (PCR and Southern blot analysis) to contain more than one event.

Transformation of GS3 maize embryos was carried out in a similar manner to sorghum and cultured on medium identical to that for sorghum for the period of the experiment. In cases where sorghum and maize embryos were infected together the procedure followed was to isolate embryos of both crops into the same tube, infect them together and either plate/spread the maize embryos and sorghum embryos separately on different plates during the co-cultivation phase, or alternatively the two types of embryos were plated adjacent and touching each other on the same plate. These groups of embryos were only separated after two days post infection or at the end of the co-cultivation period (3 days post infection). Before assaying for GFP expression sorghum embryos were separated from maize embryos.

Figure 2:
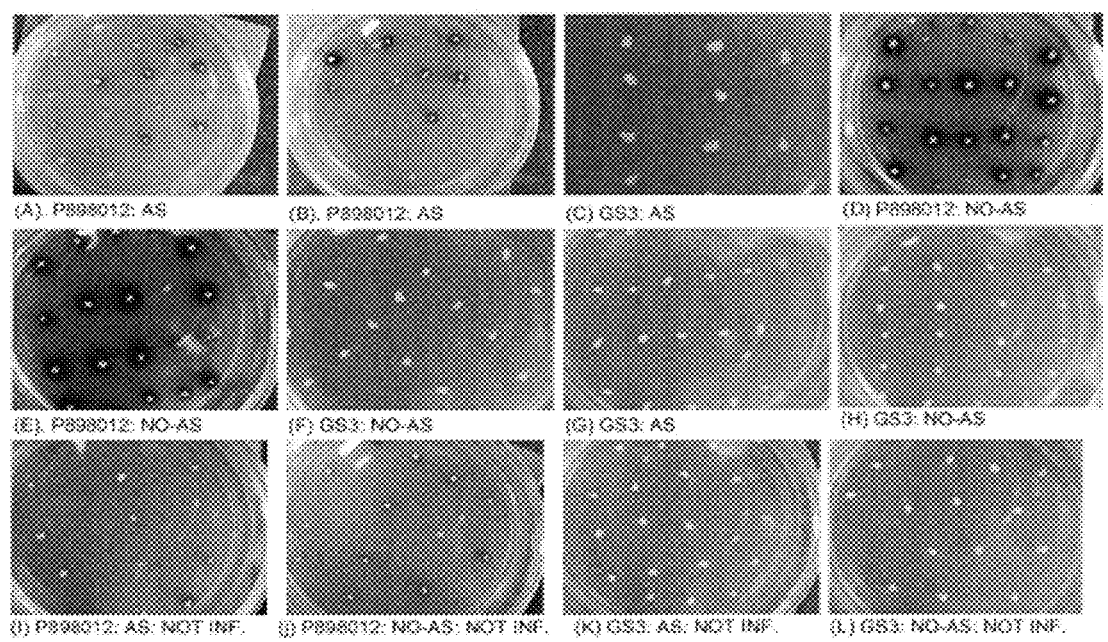
FIG. 2: Effect of including or excluding synthetic acetosyringone on phenolic compound production by sorghum (P898012) and maize (GS3) immature embryos after 2-3 days of culture. "AS" or "NO-AS" indicates infection and co-cultivation in the presence or absence of acetosyringone respectively. "NOT INF." Indicates embryos that have not been infected and are used as internal controls. P898012 and GS3 embryos in (B-C) and in (E-F) were isolated into the same tube, infected together and then only plated separately for co-cultivation.

Cultured immature zygotic embryos of the sorghum genotype P898012 produce phenolic compounds which can be visually identified as black/dark brown exudates within the proximity of the embryos on tissue culture medium (FIG. 2 (I) and FIG. 1 (J)). When these immature embryos are infected with *A. tumefaciens*, higher quantities of these phenolic compounds are produced, especially when the medium on which the embryos are cultured is not supplemented with the synthetic acetosyringone (contrast FIGS. 2 (A & B) vs. FIGS. 2 (D & E)).

Immature zygotic embryos of the GS3 maize genotype used in this research do not produce visible phenolic compounds in tissue culture, whether they have been infected with *Agrobacterium* or not (FIG. 2 (C, F, G, H, K, L)).

Figure 3:
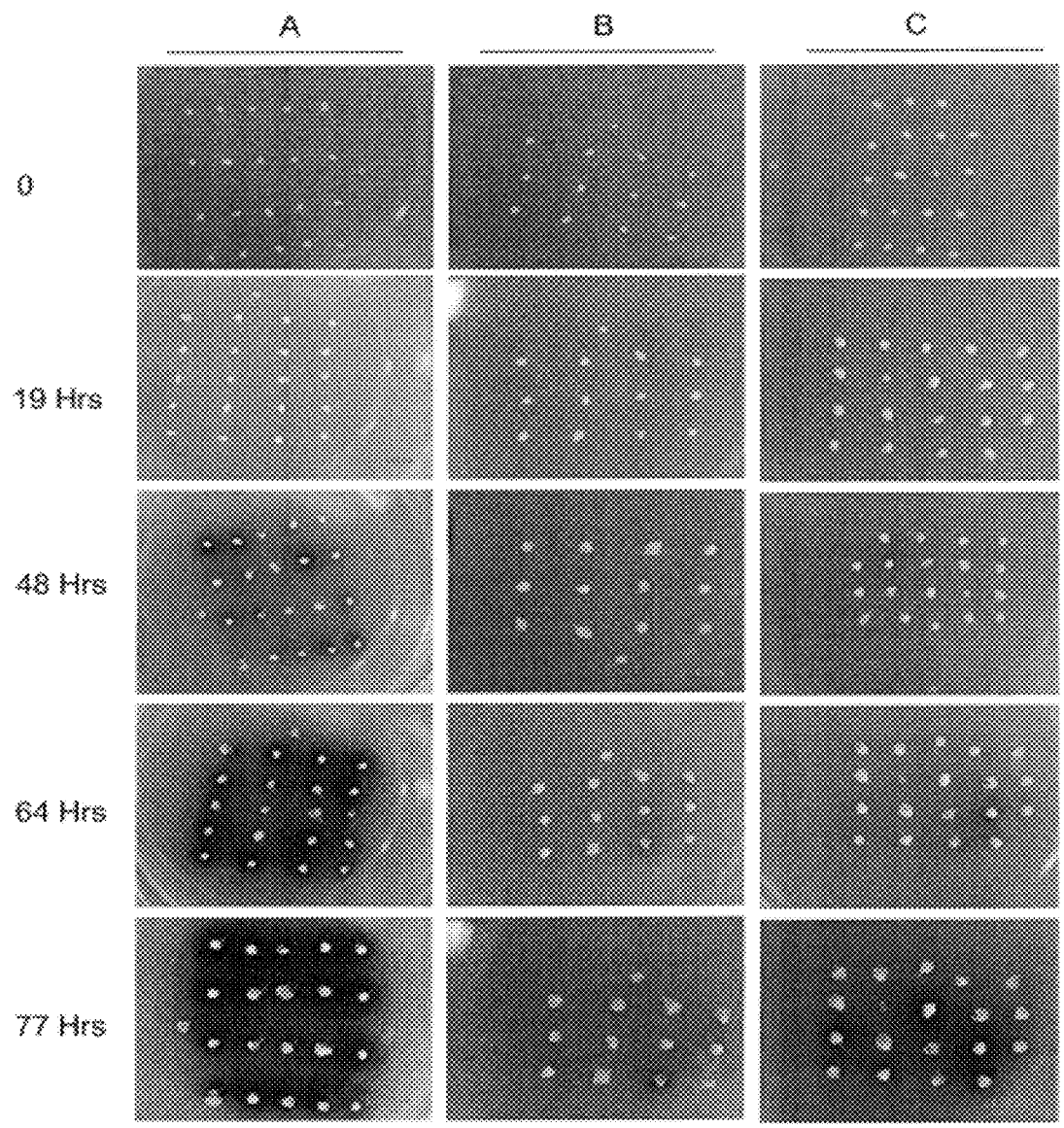
FIG. 3: Phenolic compound production in P898012 sorghum immature embryos infected with *Agrobacterium* vector PHP15303. (A). No acetosyringone was used in infection medium 700 and co-cultivation medium 710B. (B). 100 μM acetosyringone was used in infection medium 700 and in co-cultivation medium 710B. (C). 2000 μM of acetosyringone was used in infection medium 700 and 100 μM acetosyringone in 710B. Time (hours) since infection is recorded on the left of the photographs.

The use of synthetic acetosyringone depresses the production of phenolic compounds in infected and cultured immature zygotic embryos of sorghum (FIG. 3). In the absence of synthetic acetosyringone, the onset of heavy phenolic compound production or other compound production is as early as 48 hours post infection (compare FIG. 3 (panel A) vs. FIG. 3 (panel B and C)).

Phenolic compounds or other compounds produced by infected immature zygotic embryos of sorghum positively influence T-DNA transfer during the infection phase of *A. tumefactions*. Furthermore, the effect of these sorghum phenolic compounds or other compounds is additive to that of acetosyringone in promoting T-DNA transfer particularly in maize. The fact that T-DNA transfer was achieved in the absence of synthetic acetosyringone is proof that sorghum phenolic compounds or other compounds are capable of activating the vir genes of *Agrobacterium* and are a sufficient signal for the processing and transfer of T-DNA. The T-DNA transfer induced by sorghum phenolic compounds or other compounds is equivalent in intensity to that effected by the exogenous acetosyringone.

Figure 4:
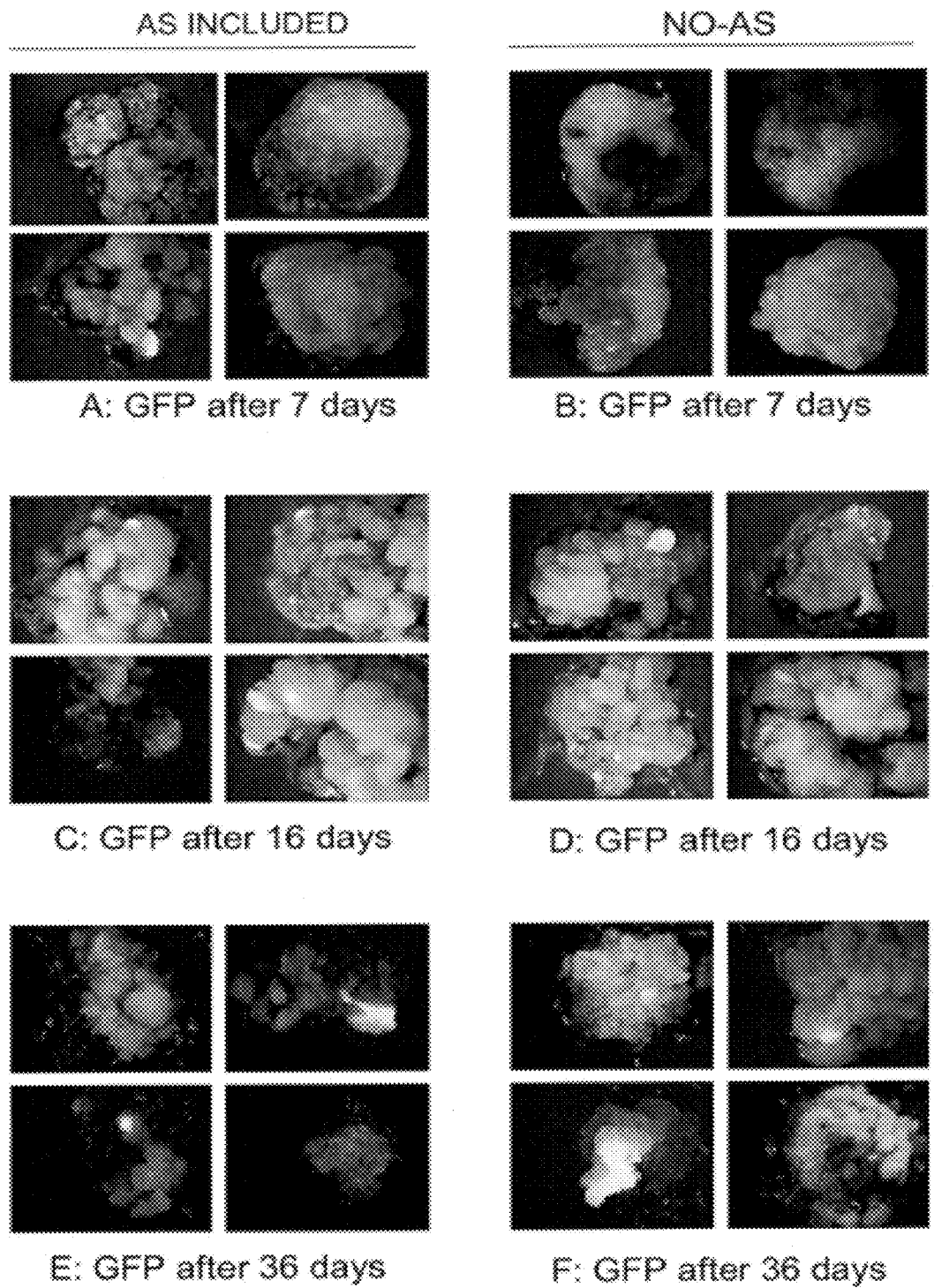
FIG. 4: Stable transformed sorghum calli were obtained following omission or inclusion of the synthetic acetosyringone. This is proof that sorghum phenolic compounds are capable of effecting permanent T-DNA transfer. White sectors and spots indicate stable GFP expression.

Sorghum phenolic compounds are capable of effecting permanent T-DNA transfer and hence stable foreign DNA integration (FIG. 4). In order for T-DNA transfer to occur, there must be a transducer and activator of the vir genes of *Agrobacterium* in the manner of the two-component system involving virA/virG. These results indicate that sorghum phenolic compounds or other compounds can be used as potent signals for the transcriptional activation of the vir genes of

*Agrobacterium*. This effectively means that these phenolic compounds or other compounds can be used to extend the current repertoire of compounds that can be used across many different crop species to improve the process of *Agrobacterium*-mediated transformation.

It was also shown that the effect of sorghum phenolic compounds or other compounds is synergistic to the synthetic acetosyringone (FIG. 3 (C)).

The results obtained in this research indicate that it is possible that phenolic compounds or other compounds produced by wounded immature embryos of sorghum can be efficiently employed to enhance or substitute for acetosyringone or other transformation-inducing compounds when *Agrobacterium* is used for transforming cereals such as sorghum, corn, rice, wheat and barley.

References

The following references are included herein by reference:

Roy, M. Jain, R. K., Rohila, J. S. and Wu. R. 2000. Production of agronomically superior transgenic rice plants using *agrobacterium* transformation methods: present status and future perspectives. *Curr. Scie.* 79 (9): 954-960.

Shimoda, N., Akiko, T-Y., Nagamine, J., Usami, S. Katayama, M., Sakagami, Y. and Machida, Y. 1990. Control of expression of *Agrobacterium* vir genes by synergistic actions of phenolic signal molecules and monosaccharides. *PNAS* 87: 6684-6688.

Spencer, P. A. and Towers, G. H. N. 1991. Restricted occurrence of acetophenone signal compounds. *Phytochem.* 27: 2781-2785.

Zhao, Z. Y., Cai, T., Tagliani, L., Miller, M., Wang, N., Pang, H., Rudert, M., Schroeder, S., Hondred, D., Seltzer, J. and Pierce, D. 2000. *Agrobacterium*-mediated sorghum transformation. *Plant Mol. Biol.* 44: 789-798.

Zhu, J., Oger, P. M., Schrammeijer, Hooykaas, P. J. J, Farrand, S. and Winans, S. C. 2000. The bases of crown gall tumorigenesis. *J. Bacteriol.* 182: 3885-3895.

What is claimed is:

1. A method of *Agrobacterium*-mediated sorghum transformation, which comprises:
   stimulating a sorghum immature embryo wounding to produce an endogenous phenolic compound which induces a virulence gene, which stimulation occurs in the absence of exogenously applied acetosyringone or other transformation-inducing phenolic compounds; and
   exposing the *Agrobacterium* to the stimulated embryo and the endogenous phenolic compound.

2. The method according to claim 1, wherein the *Agrobacterium* is *Agrobacterium tumefaciens*.

3. The method according to claim 1, wherein expression of the virulence gene is up-regulated.

4. The method according to claim 3, wherein the virulence gene which is up-regulated is the vir-A and/or vir-G gene.

5. The method according to claim 1, wherein cells of the sorghum immature embryo exposed to the *Agrobacterium* and the endogenous phenolic compound are transformed with T-DNA from the *Agrobacterium*.

6. The method according to claim 1, which is performed in the absence of exogenous sinapinic acid, syringic acid, vanillin, ferulic acid, 3,4 dihydroxy-benzoic acid, catechol, p-hydroxy-benzoic acid, vanyllyl alcohol, 3,4 dihydroxy-benzalhyde, vanillic acid or isovanillic acid.

7. A method of *Agrobacterium*-mediated sorghum transformation, which comprises:
   stimulating a sorghum immature embryo by a method selected from the group consisting of wounding, centrifuging, sonicating, heat shocking, vortexing and chemical wounding to produce an endogenous phenolic compound which induces a virulence gene, which stimulation occurs in the absence of exogenously applied acetosyringone or other transformation-inducing phenolic compounds; and
   exposing the *Agrobacterium* to the stimulated embryo and the endogenous phenolic compound.

8. The method according to claim 7, wherein the sorghum immature embryo is stimulated by vortexing.

9. The method according to claim 7, wherein the *Agrobacterium* is *Agrobacterium tumefaciens*.

10. The method according to claim 7, wherein expression of the virulence gene is up-regulated.

11. The method according to claim 10, wherein the virulence gene which is up-regulated is the vir-A and/or vir-G gene.

12. The method according to claim 7, wherein cells of the sorghum immature embryo exposed to the *Agrobacterium* and the endogenous phenolic compound are transformed with T-DNA from the *Agrobacterium*.

13. The method according to claim 7, which is performed in the absence of exogenous sinapinic acid, syringic acid, vanillin, ferulic acid, 3,4 dihydroxy-benzoic acid, catechol, p-hydroxy-benzoic acid, vanyllyl alcohol, 3,4 dihydroxy-benzalhyde, vanillic acid or isovanillic acid.

14. A method of *Agrobacterium*-mediated sorghum transformation, which comprises:
   stimulating a sorghum immature embryo via vortexing to produce an endogenous phenolic compound which induces a virulence gene, which stimulation occurs in the absence of exogenously applied acetosyringone or other transformation-inducing phenolic compounds; and
   exposing the *Agrobacterium* to the stimulated embryo and the endogenous phenolic compound.

15. The method according to claim 14, wherein the *Agrobacterium* is *Agrobacterium tumefaciens*.

16. The method according to claim 14, wherein expression of the virulence gene is up-regulated.

17. The method according to claim 16, wherein the virulence gene which is up-regulated is the vir-A and/or vir-G gene.

18. The method according to claim 14, wherein cells of the sorghum immature embryo exposed to the *Agrobacterium* and the endogenous phenolic compound are transformed with T-DNA from the *Agrobacterium*.

19. The method according to claim 14, which is performed in the absence of exogenous sinapinic acid, syringic acid, vanillin, ferulic acid, 3,4 dihydroxy-benzoic acid, catechol, p-hydroxy-benzoic acid, vanyllyl alcohol, 3,4 dihydroxy-benzalhyde, vanillic acid or isovanillic acid.

* * * * *